US00PP33038P3

(12) United States Plant Patent
Ferreira

(10) Patent No.: US PP33,038 P3
(45) Date of Patent: May 11, 2021

(54) MANDARIN TREE NAMED 'PATENSIE EARLY'

(50) Latin Name: *Citrus reticulata*
Varietal Denomination: Patensie Early

(71) Applicant: CITRIGENE (Pty) Ltd, Humansdorp (ZA)

(72) Inventor: Gert Ferreira, Patensie (ZA)

(73) Assignee: CITRIGENE (Pty) Ltd, Humansdorp (ZA)

( * ) Notice: Subject to any disclaimer, the term of this patent is extended or adjusted under 35 U.S.C. 154(b) by 0 days.

(21) Appl. No.: 16/501,343

(22) Filed: Mar. 27, 2019

(65) Prior Publication Data

US 2020/0315078 P1 Oct. 1, 2020

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./202
CPC ..... A01H 6/785
See application file for complete search history.

(56) References Cited

PUBLICATIONS

"Producao de citros irrigados com agua moderademente salina," Da Silva et al., Iffiga, Botucatu, Edicao Especial, p. 396-407, 2012, ISSN 1808-3765.*

* cited by examiner

*Primary Examiner* — Anne Marie Grunberg
(74) *Attorney, Agent, or Firm* — Klarquist Sparkman, LLP

(57) ABSTRACT

A new and distinct mandarin tree characterized by a ripening 2 3 weeks earlier than 'Nadorcott', having better rind quality (e.g., smoother rind, less prone to sunburn, less ridging, firmer peel, and a lighter color with an attractive blush), and a more round shape than 'Nadorcott'.

5 Drawing Sheets

Genus and species: *Citrus reticulata.*
Variety denomination: 'PATENSIE EARLY'.

BACKGROUND OF THE INVENTION

The present invention relates to a new and distinct variety of a mandarin tree named 'Patensie Early', which originated from a spontaneous mutant of 'Nadorcott' (U.S. Plant Pat. No. 10,480). The new mandarin variety has an earlier ripening time and improved rind quality as compared to 'Nadorcott'.

SUMMARY OF THE INVENTION

The following unique combination of characteristics that are outstanding in the new mandarin variety and distinguish it from 'Nadorcott', as well as from all other varieties of which I am aware:

1. Earlier ripening (2-3 weeks earlier than 'Nadorcott') due to earlier rind color development and lower acidity;
2. Better rind quality, namely smoother rind, less prone to sunburn, less ridging (radial grooves), firmer peel, lighter color with an attractive orange blush;
3. Less flattened and more round fruit shape compared with 'Nadorcott.'.

Additional details on how the two varieties can be distinguished is shown below.

| | 'Nadorcott' | 'Patensie Early' |
|---|---|---|
| Fruit Shape | Oblate to deeply oblate; typically 0.80 H:D ratio with flatter appearance | Slightly oblate; approximately 0.85 H:D ratio of height to diameter; rounder appearance than 'Nadorcott' fruit |
| Fruit Height | ±48 mm | 37 to 53 mm |
| Fruit Diameter | ±60 mm | 42 to 62 mm |
| Fruit Stem-end | Radial grooves or ribbing are present (FIG. 5) | Ribbing is typically absent to very slight (see FIG. 5) |
| Skin Thickness | 2.8 to 3.5 mm | 2.5 to 3.0 mm |
| Rind color immature | RHS yellow-green 147B | RHS yellow-green 147B with earlier color break than 'Nadorcott' (see FIGS. 4 & 6) |
| Rind color mature | Deep orange (RHS orange N25B) with later color development than 'Patensie Early' (see FIGS 4, 5, 6); salmon pink albedo (RHS orange 24D) | Deep orange (RHS orange N25B) (see FIG. 5); salmon pink albedo (RHS orange 24D) |
| Maturity period | Late-June through early-August in South Africa | 2 to 3 weeks earlier than 'Nadorcott' due to earlier rind color and lower acidity (June 6 to July 25 in South Africa) |
| Eating quality (at maturity) | Very good at maturity, but higher acidity when 'Patensie Early' is at optimal maturity, | Typically +12°Brix and 1.0 to 1.2% acidity and comparable with 'Nadorcott' when 'Nadorcott' achieves maturity; |

-continued

| 'Nadorcott' | 'Patensie Early' |
|---|---|
| i.e., 'Nadorcote is later maturing | lower acidity than 'Nadorcott' combined with earlier color development result in earlier maturity than 'Nadorcott' |

This new cultivar has been reproduced only by asexual propagation (by budwood), in Patensie, Eastern Cape South Africa. Each of the progeny exhibits identical characteristics to the original plant. Asexual propagation by budwood, as done in Patensie, Eastern Cape South Africa, shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

The accompanying illustration shows typical specimens of the leaves, flowers, and fruit of this new variety depicted in color as nearly true as it is reasonably possible to make the same in a color illustration of this character.

DETAILED BOTANICAL DESCRIPTION

Figure 1:
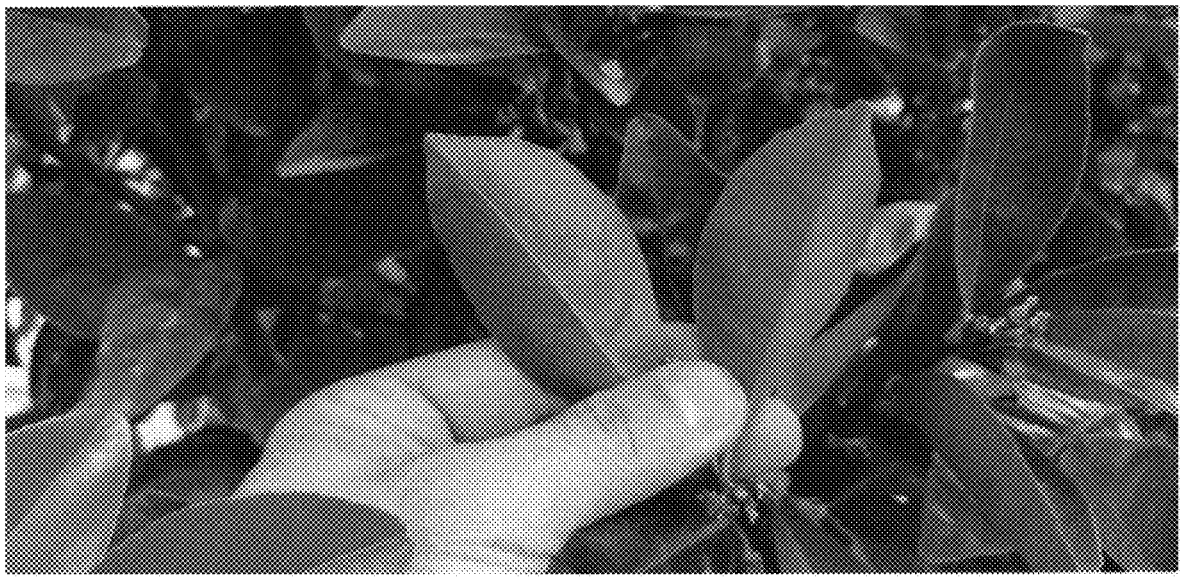
FIG. 1 shows leaves on a 'Patensie Early' tree. The leaves of 'Patensie Early' are similar in leaf shape and size, but slightly paler in color, compared with leaves of 'Nadorcott' under the same condition.
Figure 2:
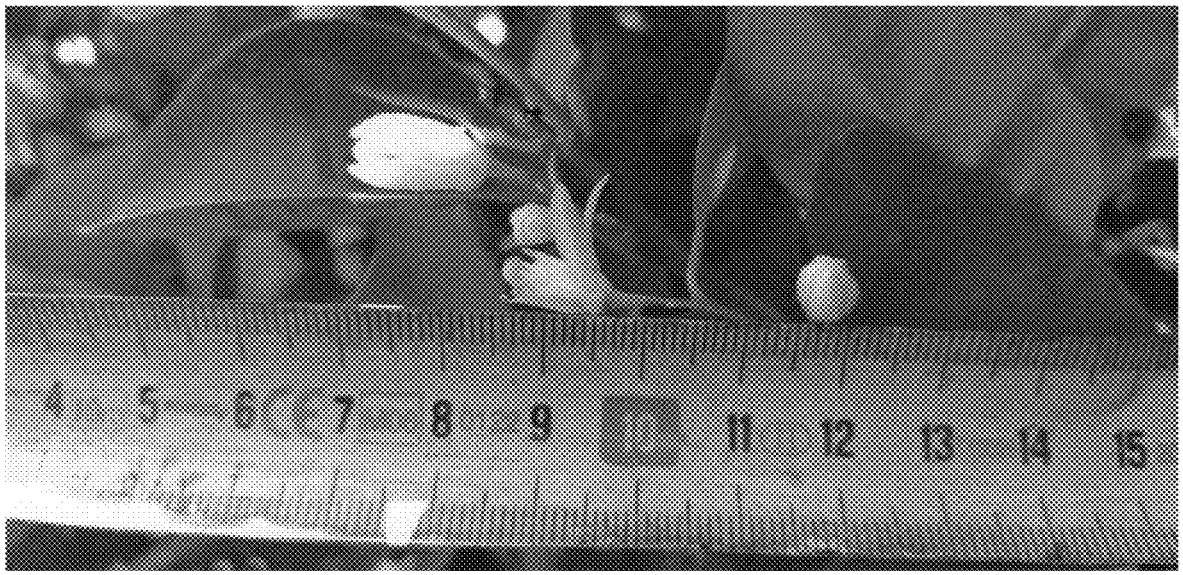
FIG. 2 shows flowers on a of 'Patensie Early' tree, which are similar to those found on 'Nadorcott'.
Figure 3:
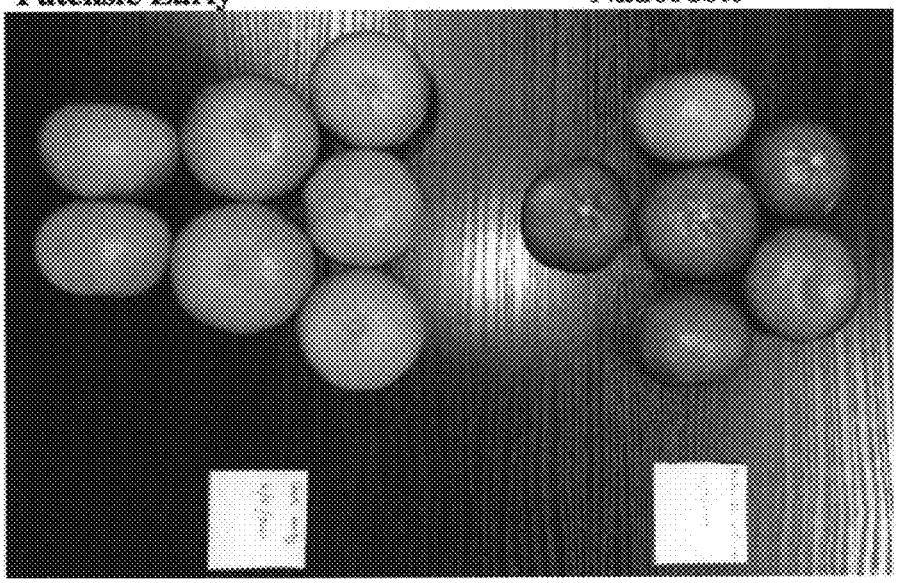
FIG. 3 shows fruit from 'Patensie Early' and 'Nadorcott' trees, demonstrating the earlier rind color development of 'Patensie Early' fruit compared with 'Nadorcott' fruit under the same growing conditions.
Figure 4:
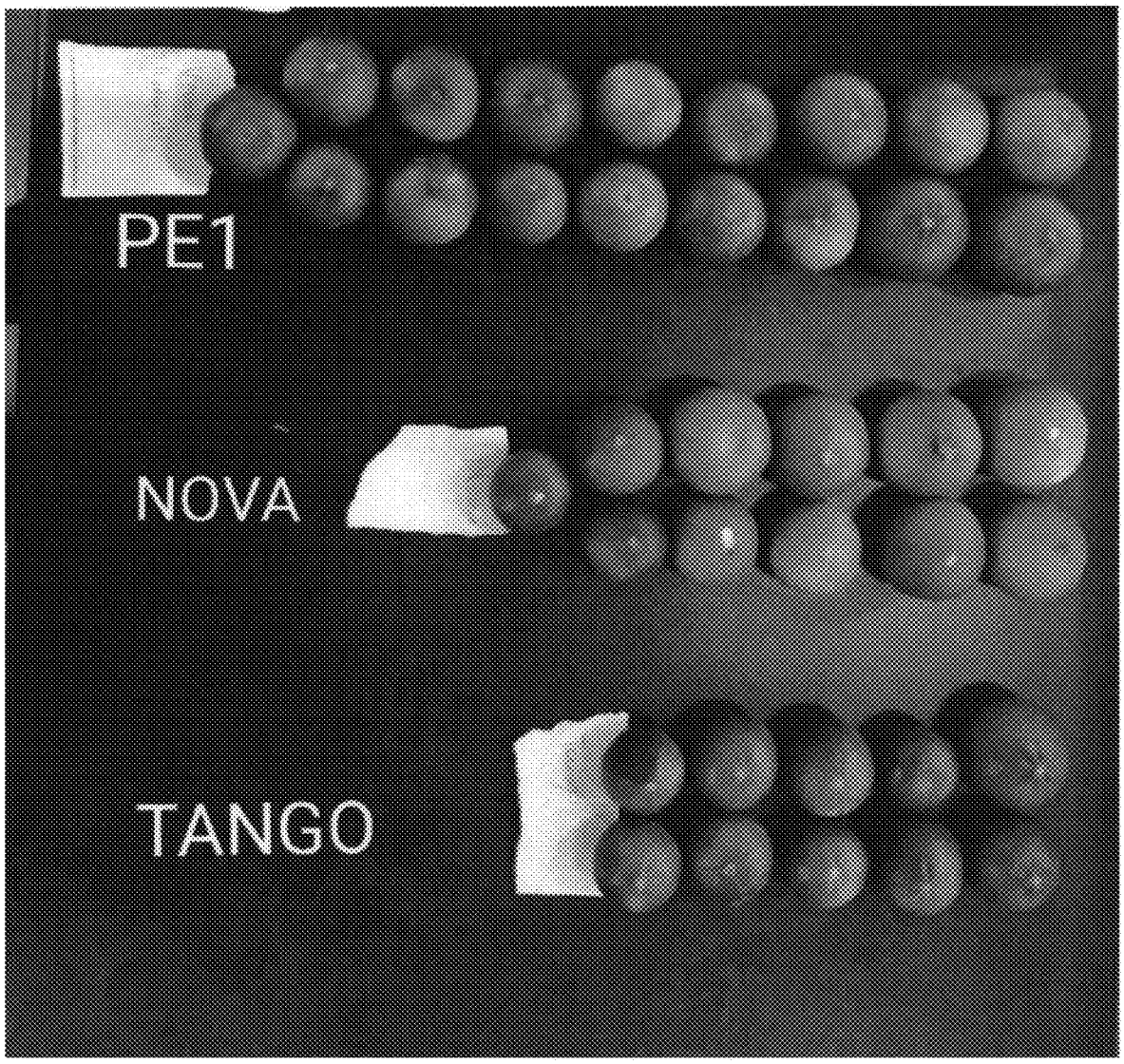
FIG. 4 shows fruit from 'Patensie Early', 'Nova' (unpatented) and 'Tango' (U.S. Plant Pat. No. 17,863) trees, demonstrating the early color break of the rind of 'Patensie Early' compared with 'Tango', but similar to 'Nova'.
Figure 5:
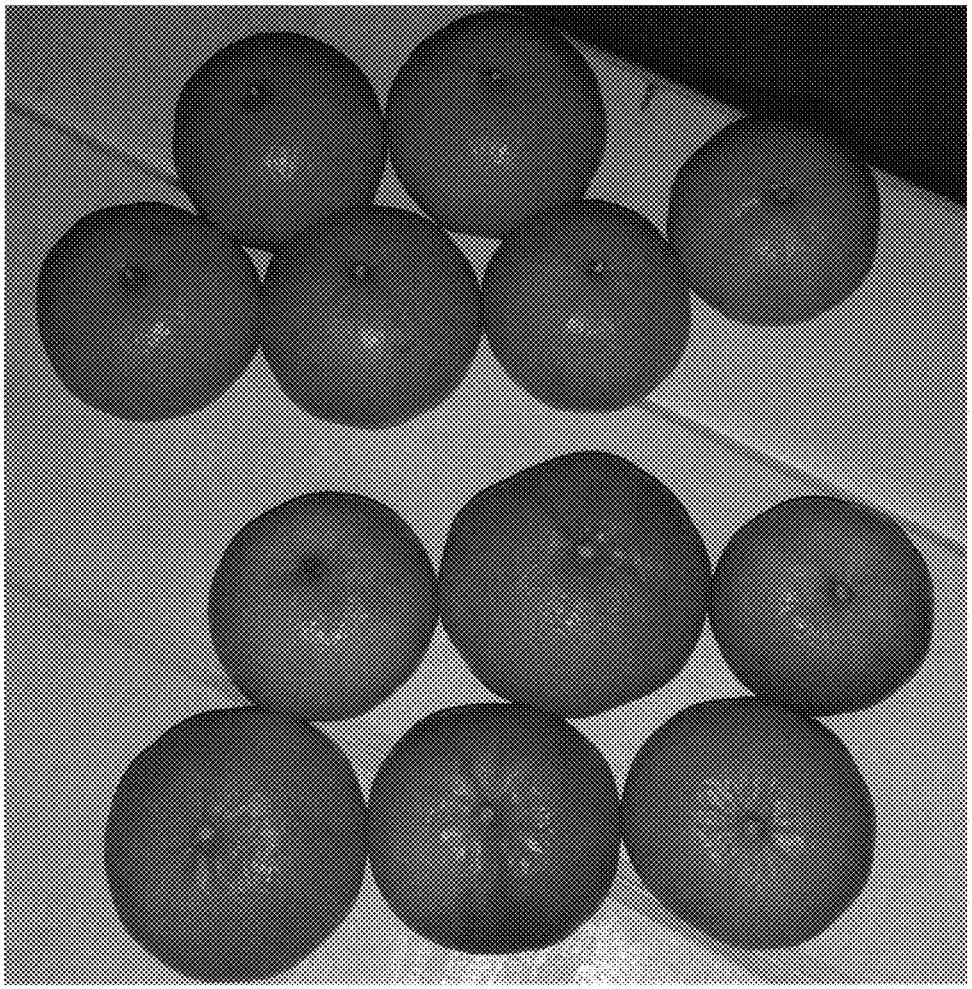
FIG. 5 shows fully mature fruit from 'Patensie Early' (upper) and 'Nadorcott' (lower) trees, demonstrating the earlier rind color development of 'Patensie Early' fruit compared with 'Nadorcott' fruit under the same growing conditions as well as less ribbing/radial grooves.
Figure 6:
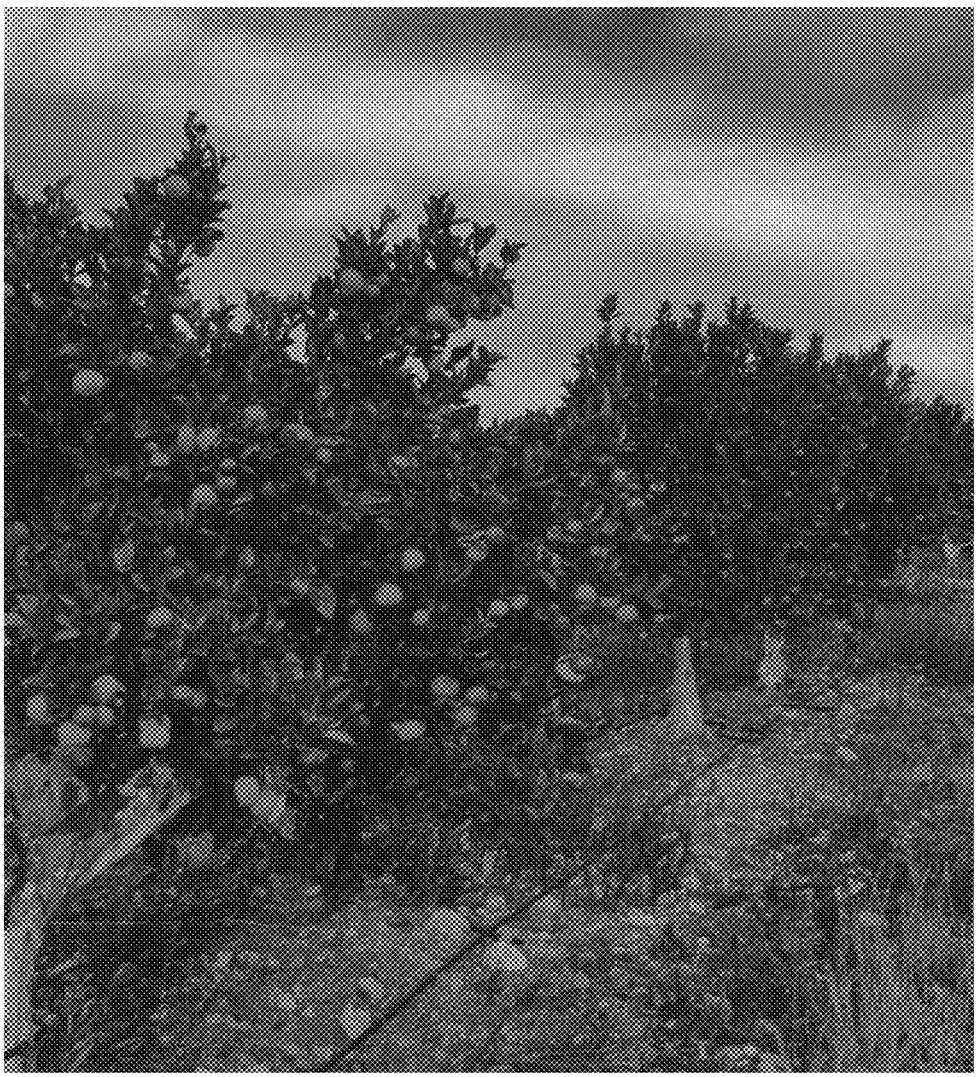
FIG. 6 shows 'Patensie Early' trees in a trial plot in Patensie, Eastern Cape Province, South Africa.

The following is a detailed description of the new mandarin based on observations taken of a 5 year-old specimen grown in trial beds outside in full sun in Patensie, Eastern Cape South Africa. The color descriptions are all based on The *Royal Horticultural Society Colour Chart,* $5^{th}$ edition, 2007.

Parentage: Spontaneous mutation of 'Nadorcott'.

Tree:

*Ploidy*.—Dipolid.
*Size*.—Same as 'Nadorcott'.
*Height*.—3.5 m.
*Tree spread*.—2.3 m.
*Vigor*.—Strong.
*Density*.—Open to medium, similar to 'Nadorcott' mandarin.
*Form*.—Generally upright in the first 4 years followed by a tendency to grow into more spherical shape in the following years, similar to 'Nadorcott' mandarin.

Trunk:

*Trunk diameter*.—17 cm in diameter at a height of 35 cm above the ground, 5 year old tree.
*Trunk texture*.—Smooth, similar to 'Nadorcott' mandarin.
*Trunk bark color*.—RHS grey-brown N199A, similar to 'Nadorcott' mandarin.

Branches:

*Branch length*.—400 mm.
*Branch diameter*.—170 mm.
*Branch texture*.—Smooth.
*Branch color*.—RHS grey-brown N199A.
*Strength*.—Strong.
*Thorniness*.—Typically absent, rarely short spines (3 to 6 mm in length).

Roots: The roots are on rootstock Swingle Citrumelo.

Leaves:

*Size* (*lamina average*).—Length: 78 mm. Width: 34.3 mm.
*Leaf cross-section*.—Concave.
*Shape*.—Elliptical.
*Apex*.—Acute to obtuse with occasional and slight emargination.
*Margin*.—Crenate.
*Margin undulation*.—Not typically undulated.
*Surface*.—Upper surface: smooth. Lower surface: smooth.
*Leaf blade twisting or blistering*.—Does not typically occur.
*Color*.—Upper surface (apaxial): RHS green 137A. Lower surface (abaxial): RHS yellow-green 146B; the leaves of 'Patensie Early' are similar in leaf shape and size, but slightly paler in color compared with leaves of 'Nadorcott' under the same condition.
*Petiole*.—Occasionally a small petiole is present; Length: 9.2 mm. Diameter: 1.4 mm. Color: RHS Green 137C.
*Petiole wings*.—Typically absent.

Flowers and flower buds:

*Type*.—Clustered influorescent type.
*Bearing*.—Once per year.
*Flower diameter*.—6 mm.
*Flower height*.—13 mm.
*Flower blooming period*.—First bloom: Observed August 15, Full bloom: Observed September 20 in Eastern Cape Province, Patensie.
*Number of flowers*.—Normal single and cluster, same as 'Nadorcott'.
*Color*.—RHS green-white 1570.
*Calyx*.—3 to 5 mm in diameter.
*Petal length and width*.—10 to 13 mm×4 to 6 mm.
*Petal color*.—RHS Green-White 157C.
*Anther color*.—RHS Yellow-Orange 15C.
*Pollen*.—'Patensie Early' pollen is viable and capable of cross-pollinating compatible varieties.
*Style length*.—6 to 8 mm.
*Stamen length*.—8 to 12 mm.

Rostellum:

*Length*.—6 mm.
*Thickness*.—1 mm.
*Color*.—RHS Green 137A.

Fruit:

*Fruit clustering* (*infructescence*).—Does not typically occur, but occasionally fruit may set in clusters of 2 to 3 fruit, rarely more.

*Size*.—Uniform.

*Shape*.—Slightly oblate, approximately 0.85 ratio of height to width; less oblate and more round than 'Nadorcott' mandarin fruit; the broadest part of the fruit is in the middle (equator) of the fruit.

*Tall*.—37 to 53 mm.

*Width*.—42 to 62 mm.

*Average weight* (*per individual fruit*).—90 g.

*Texture*.—The fruit surface is smooth and glossy, similar to 'Nadorcott' mandarin fruit, except with less ribbing/radial grooves at the stem-end than 'Nadorcott' fruit.

*Oil glands*.—The oil glands are conspicuous, slightly depressed to flat, and of similar size with some larger oil glands interspersed among them; there is no pebbling or pitting on the fruit oil glands.

*Fruit collar*.—Absent.

*Abscission layer between the floral disc and the fruit*.—The floral disc or calyx tightly adheres to the fruit and is green in color (RHS Green 137A).

*Stylar-end*.—Slightly depressed stylar end with no navel or stylar opening but an obvious areola; the stylar scar is small, approximately 1 mm in diameter.

*Style*.—Non-persistent.

*Areola*.—Faint and smooth, 8 to 12 mm in diameter.

*Color*.—RHS orange N25B when fully mature, green fruit is RHS yellow-green 147B; early color development than 'Nadorcott'.

*Harvesting*.—First pick around October 6 (based on season and rootstock); last pick around July 25 (based on season and rootstock), in South Africa, Eastern Cape Province, Patensie. Approximately 3 weeks earlier than 'Nadorcott' under the same growing conditions.

*Productivity*.—Good (30 to 50 kg per tree on 4- and 5-year-old trees), similar to 'Nadorcott'.

*Parthenocarpy*.—'Patensie Early' exhibits parthenocarpic fruit set ability.

*Self-incompatibility*.—'Patensie Early' is self-incompatible, producing seedless fruit in the absence of cross-pollination.

Fruit skin:

*Adherence*.—Easy peeling when fruit are mature.

*Thickness*.—2.5 to 3.0 mm; typically slightly thinner than 'Nadorcott' mandarin.

*Texture*.—Smooth with less ribbing/radial grooves at the stem-end compared with 'Nadorcott' fruit which typically have ribbing at the stem-end.

*Color*.—Earlier rind color development compared with 'Nadorcott'; Flavedo (epicarp) orange when fully mature (RHS orange N25B); Albedo (mesocarp): RHS orange 24D.

*Albedo density*.—Medium.

*Albedo adherence*.—Upon peeling the fruit, very little albedo adheres to the outer segment walls, however, typically one albedo strand per fruit segment remains.

Fruit flesh:

*Flesh* (*pulp*) *texture*.—Smooth.

*Flesh* (*pulp*) *color*.—RHS orange-red N30D.

*Central core*.—Closed.

*Number of segments*.—9 to 11 fully developed segments which are easily separated from one another; rudimentary segments are typically absent.

*Segment walls*.—Tender.

*Internal navel*.—Absent.

*Juice vesicles*.—Vary in length according to fruit size; typically 20 to 30 mm.

*Juice content*.—Typically +50% when fully mature.

*Eating quality*.—Typically +12° Brix and 1.0 to 1.2% acidity at maturity with lower acidity than 'Nadorcott' when 'Patensie Early' is at optimal fruit maturity.

Seeds:

*Number*.—Zero when not cross pollinate by compatible pollen; numerous seeds when cross-pollinated by compatible pollen.

*Embryony*.—Polyembryonic.

*Texture*.—Smooth.

*Seed coat color*.—Grey-yellow 162D, similar to 'Nadorcott'.

*Cotyledon color*.—Greyed-yellow 163D, similar to 'Nadorcott'.

*Length and width*.—10 to 12 mm×3 mm.

I claim:

1. A new and distinct variety of mandarin tree, substantially as herein shown and described.

* * * * *

'Patensie Early' 'Nadorcott'